United States Patent
Backus et al.

(10) Patent No.: US 11,606,648 B2
(45) Date of Patent: Mar. 14, 2023

(54) CHARGING AND UPDATING OF AN IMPLANTABLE HEARING AID

(71) Applicant: Oticon Medical A/S, Smørum (DK)

(72) Inventors: Bradford Backus, Vallauris (FR);
Régis Pierquin, Vallauris (FR)

(73) Assignee: Oticon Medical A/S, Smørum (DK)

( * ) Notice: Subject to any disclaimer, the term of this patent is extended or adjusted under 35 U.S.C. 154(b) by 247 days.

(21) Appl. No.: 16/778,980

(22) Filed: Jan. 31, 2020

(65) Prior Publication Data

US 2021/0243532 A1  Aug. 5, 2021

(51) Int. Cl.
*H04R 25/00* (2006.01)

(52) U.S. Cl.
CPC ........... *H04R 25/30* (2013.01); *H04R 25/554* (2013.01); *H04R 25/606* (2013.01); *H04R 2225/67* (2013.01)

(58) Field of Classification Search
CPC ...... H04R 25/554; H04R 25/00; H04R 25/55; H04R 25/30; H04R 25/606; H04R 25/60; H04R 25/602; H04R 25/603; H04R 25/609; H04R 2225/67; H04R 2225/31; H04R 2225/51; H04R 2225/61; H04R 2225/55; H04R 2225/33; A61B 5/0002–0031; H02J 50/10; H02J 2310/23; H02J 7/04; H02J 13/00022; H02J 50/12; H02J 50/80; H02J 7/00034; H02J 7/00308; H02J 7/007; H04B 5/0031; H04B 5/0037; H04B 5/0081; H04B 5/0075; A61N 1/36038; A61N 1/37223; A61N 1/3787

USPC .......................................................... 600/25
See application file for complete search history.

(56) References Cited

U.S. PATENT DOCUMENTS

| | | | | |
|---|---|---|---|---|
| 5,279,292 A | * | 1/1994 | Baumann | H02J 50/005 607/57 |
| 10,511,189 B2 | | 12/2019 | Ridler et al. | |
| 2002/0071581 A1 | * | 6/2002 | Leysieffer | H04R 25/606 381/312 |
| 2005/0017673 A1 | * | 1/2005 | Tsukamoto | H02J 50/10 320/106 |

(Continued)

FOREIGN PATENT DOCUMENTS

EP  3001700 A1 *  3/2016  ........... H04R 25/604

OTHER PUBLICATIONS

Extended European Search Report for European Application No. 21152525.8, dated Jun. 14, 2021.

*Primary Examiner* — Sunita Reddy
(74) *Attorney, Agent, or Firm* — Birch, Stewart, Kolasch & Birch, LLP (57) ABSTRACT

An implantable hearing aid system is disclosed. According to one or more of the mentioned aspects, the implantable hearing aid system comprises a charger unit which includes a coil unit having a first resonance frequency, a hearing aid and an implantable component. The hearing aid includes a rechargeable battery, an inductive coil arrangement having a second resonance frequency configured to form an inductive charging link with the coil unit to receive power signals from the charger unit. The implantable component includes an implantable coil, wherein the inductive coil arrangement may further be configured to form a transcutaneous link with the implantable coil to transmit at least one of data and power to the implantable component.

17 Claims, 5 Drawing Sheets

(56) References Cited

U.S. PATENT DOCUMENTS

| | | | |
|---|---|---|---|
| 2007/0195965 A1* | 8/2007 | Thomasson | H04R 25/70 381/60 |
| 2010/0137948 A1* | 6/2010 | Aghassian | H02J 50/80 607/61 |
| 2011/0112610 A1* | 5/2011 | Rahman | A61N 1/37211 607/60 |
| 2012/0170781 A1* | 7/2012 | Klemenz | H02J 50/12 381/323 |
| 2014/0114373 A1 | 4/2014 | Aghassian | |
| 2014/0152251 A1* | 6/2014 | Kim | H02J 50/12 320/108 |
| 2015/0380972 A1* | 12/2015 | Fort | H02J 50/80 320/108 |
| 2016/0241063 A1* | 8/2016 | Hatanaka | H04R 25/607 |
| 2017/0040841 A1 | 2/2017 | Ridler et al. | |
| 2017/0180886 A1* | 6/2017 | Van Der Loo | H04W 12/06 |
| 2018/0063655 A1* | 3/2018 | Case | H04R 25/606 |
| 2018/0124529 A1* | 5/2018 | Larsen | H04R 25/00 |
| 2018/0272131 A1* | 9/2018 | Meskens | A61N 1/3787 |
| 2020/0374638 A1* | 11/2020 | Oplinger | H04R 25/554 |

\* cited by examiner

CHARGING AND UPDATING OF AN IMPLANTABLE HEARING AID

FIELD

The present disclosure relates to an implantable hearing aid system for charging and updating a hearing aid via an inductive coil arrangement.

BACKGROUND

An implantable hearing aid system for improving a hearing-impaired person's capability to hear may impose either electrical stimulation of a cochlea of the person or vibration applied on to the skull of the person, or a combination of the electrical stimulation and vibration. In most cases, the implantable hearing aid system includes a hearing aid, such as an external component, placed on or at the head of the person and an implantable component arranged between the skin and the skull of the person. The implantable component applies the electrical stimulation and/or the vibration. In any of the mentioned cases, a rechargeable battery may be arranged in the hearing aid, and in that case, a charger is needed for recharging the rechargeable battery. There exists a variety of conventional wireless technology standards for charging Li-Ion and other batteries which today becomes more accessible in the way of being built into furniture, electronic articles, and other elements that are around us. An example of a conventional wireless technology standard is the QI standard which defines a wireless power transfer using inductive charging.

Thus, it is known to make a charger configured for recharging a rechargeable battery of an implantable hearing aid when reading US 2017/0040841 A1, however, the disadvantage with the disclosed solution is that the charger is not part of a conventional wireless technology standard, as for example the QI standard, instead the charger is customized specifically for a specific implantable hearing aid. Thereby, the likelihood of being able to recharge the disclosed implantable hearing aid is significantly less when your away from home and have not brought the customized charger with you.

Thereby, it is a need for having an implantable hearing aid which is configured to be recharged via a conventional wireless technology standard.

SUMMARY

An aspect of the disclosure is to provide an implantable hearing aid system which applies recharging of a hearing aid via a conventional wireless technology standard for improving the accessibility to a charger unit when being away from home.

A further aspect of the disclosure is to provide an implantable hearing aid system which applies software updating of a hearing aid via an inductive coil arrangement also used for recharging.

According to one or more of the mentioned aspects, the implantable hearing aid system comprises a charger unit which includes a coil unit having a first resonance frequency, a hearing aid and an implantable component. The hearing aid includes a rechargeable battery, an inductive coil arrangement having a second resonance frequency configured to form an inductive charging link with the coil unit to receive power signals from the charger unit. The implantable component includes an implantable coil, wherein the inductive coil arrangement may further be configured to form a transcutaneous link with the implantable coil to transmit at least one of data and power to the implantable component.

The first resonance frequency and the second resonance frequency are matched or partly matched in order for the inductive coil arrangement to be configured to receive and/or transmit data and/or power via the inductive charging link which may be part of a conventional wireless technology standard, such as the QI standard.

The inductive coil arrangement may be arranged externally to a housing including the hearing aid, and where the inductive coil arrangement is connected to the housing via a connector part which includes one or more wires.

The inductive coil arrangement may be arranged within a housing of the hearing aid.

The inductive coil arrangement may be connected to the remaining parts of the hearing aid via a connector part which includes one or more wires.

The connector part may be a flexible tube which allows the hearing aid to be placed, for example behind an ear of the user, while placing the inductive coil arrangement on the skin of the head of the user.

Furthermore, the hearing aid includes a voltage decreasing converter configured to decrease a voltage of the power signals received from the charger unit for use in charging the rechargeable battery, and a voltage increasing converter configured to increase a voltage of signals obtained from the rechargeable battery.

As the first resonance frequency and the second resonance frequency are matched or partly matched, the inductive charging link is highly effective providing more voltage than what is acceptable for a rechargeable battery in a hearing aid, and in that case, it is a need to have the voltage decreasing converter in the hearing aid for decreasing the voltage of the power signals provided by the charger unit. Thereby, the lifetime of the rechargeable battery is not shortened due to overvoltage charging.

The rechargeable battery may include lead-acid, nickel-cadmium (NiCd), nickel-metal hydride (NiMH), lithium-ion (Li-ion), or lithium-ion polymer (Li-ion polymer).

Furthermore, when the hearing aid is used for communicating with the implantable component via the transcutaneous link, the hearing aid receives voltage signals from the rechargeable battery, and in that case, the voltage of signals obtained from the rechargeable battery needs to be increased via the voltage increasing converter, otherwise, no communication and/or power transfer would be robustly and/or efficiently established via the transcutaneous link.

The first resonance frequency and the second resonance frequency are within a frequency range of between 80 kHz to 300 kHz, or between 110 kHz and 205 kHz. The hearing aid is configured to shift between the two frequency ranges based on the type of the charger unit. For example, a charger unit which operates between 80 kHz to 300 kHz is characterized as being a medium power QI charger, and a charger unit which operates between 110 KHz and 205 kHZ is characterized as being a low power QI charger. A low power QI charger delivers up to 5 watts, and a medium power QI charger delivers up to 120 watts.

So, if the user of the hearing aid has at hand a low power QI charger unit, the user is able to configure the second resonance frequency to the frequency range of 110 kHz to 205 kHZ, and vice versa, for a medium power QI charger unit. The user may shift between the two ranges via a user interface of the hearing aid or via a user interface of an external communication device, such as a smartphone, a smart watch etc.

In order to secure a stable inductive charging link between the charger unit and the hearing aid, the inductive coil arrangement may include a magnet configured to align an inductive coil of the inductive coil arrangement to the coil unit of the charger unit.

The charger unit may have, a magnet, a metal surface or a metal component which is configured to magnetically attract the magnet of the inductive coil arrangement.

The metal surface or the metal component may be arranged in a center of the coil unit, and wherein the center of the coil unit is circumference by coils of the coil unit.

The inductive coil arrangement may have a third resonance frequency being in resonance to a resonance frequency of the implantable coil, and the third resonance frequency may be within a frequency range of 4 MHz to 6.5 MHz, 4 MHz to 10 MHz, or 4 MHz to 12 MHz. The defined frequency ranges are suitable for establishing a transcutaneous link and not for establishing an inductive charging link which may be part of a conventional wireless technology standard, such as the QI standard.

The hearing aid may include a capacitive circuit arrangement configured to adjust the resonance frequency of the inductive coil arrangement to a plurality of resonance frequencies including at least the second resonance frequency. The capacitive circuit arrangement may be connected to the inductive coil arrangement, the voltage decreasing converter and the voltage increasing converter.

The capacitive circuit arrangement may include a plurality of capacitors, and where one or more capacitor of the plurality of capacitors has a contact configured to couple and decouple the one or more capacitor, such that when the capacitor is decoupled, the capacitor is not actively part of the capacitive circuit arrangement, and when the capacitor is coupled, the capacitor is actively part of the capacitive circuit arrangement.

Position of the contact may be controlled based on a measure of a Q factor of the inductive coil arrangement or based on a power level measure of a signal received by the inductive coil arrangement.

Position of the contact for the one or more capacitors may be controlled by selecting a resonance frequency via a user interface of the hearing aid or of an external communication device, such as a smartphone, a smartwatch etc.

The hearing aid may include a processor configured to transmit a control signal to the capacitive circuit arrangement, and wherein the capacitive circuit arrangement includes a switch, a first tuning circuit and at least a second circuit, and each of the two tuning circuits may be connected to the switch, and the switch may be configured to receive the control signal, and wherein the switch may be configured to connect the inductive coil arrangement to either the first tuning circuit or the second tuning circuit based on the control signal. Thereby, the hearing aid's ability to adjust the resonance frequency of the inductive coil arrangement is improved.

The processor may be part of an external communication device, such as a smartphone, a smart watch etc.

The first tuning circuit may be configured to form the transcutaneous link with the implantable coil when connected to the inductive coil arrangement via the switch, and the second tuning circuit may be configured to form the inductive charging link with the coil unit when connected to the inductive coil arrangement via the switch.

The control signal may be determined based on a measure of a Q factor of the inductive coil arrangement, or the control signal is determined based on a power level measure of a signal received by the inductive coil arrangement.

The control signal may be determined based on a user interface of the hearing aid or an external communication device.

By being able to determine the control signal and/or the position of the contacts by the measure of the Q factor or by the measure of the power level allows for an automatically adjustment of resonance frequency of the inductive coil arrangement.

By being able to determine the control signal and/or the position of the contacts by an input via the user interface allows a simpler solution for adjusting the resonance frequency of the inductive coil arrangement.

The hearing aid may include a first antenna configured to form a communication link to a second antenna of the charger unit for communicating charging data. The communication link may be based on Bluetooth or Bluetooth low energy. The charging data may include charge capacity information or temperature of the rechargeable battery The charger unit may be configured to transmit data to the hearing aid via the inductive charging link or via a second inductive link between the coil unit and the inductive coil arrangement, and wherein the transmitted data includes charging data, software update data and/or firmware update data. Thereby, it is possible to update the software or firmware of the hearing aid while being charged. This allows the possibility of updating the hearing aid at home. Furthermore, utilizing the inductive coil arrangement secures a more compact solution of the hearing aid while reusing the inductive coil arrangement for multiple purposes. Furthermore, if using a second antenna for updating the hearing aid, the hearing aid is in need for using power from the battery for driving the second antenna, and that results in a longer charging time. Thereby, utilizing the inductive coil arrangement for multiple purposes, such as charging and updating, would result in a shorter charging time compared to the example where you have the second antenna.

The plurality of resonance frequencies may include a fourth resonance frequency for the second inductive link.

The charger unit may include a far-field communication interface configured to transmit an update acknowledgement signal via the far-field communication interface, and, to receive software update data and/or firmware update data via the far-field communication interface based on the update acknowledgement signal.

The update acknowledgement signal includes information data about the hearing aid, such as identification data.

The far-field communication interface may include a transceiver interface configured for transmitting and receiving software update data via a communication network, and wherein the communication network includes mobile network, a local network and/or a wireless network.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

DETAILED DESCRIPTION

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, etc. (collectively referred to as "elements"). Depending upon particular application, design constraints or other reasons, these elements may be implemented using other equivalent elements.

A hearing aid is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. Such audible signals may be provided in the form of an acoustic signal transferred as mechanical vibrations to the user's inner ears through bone structure of the user's head.

The hearing aid may be replaced by a system comprising one or two hearing aids, and a "binaural hearing system" refers to a system comprising two hearing aids where the devices are adapted to cooperatively provide audible signals to both of the user's ears or the hearing aid of bone conduction type may be part of a bimodal system comprising a cochlea implant and a bone conduction hearing aid. The system may further include auxiliary device(s) that communicates with at least one hearing aid, the auxiliary device affecting the operation of the hearing aids and/or benefitting from the functioning of the hearing aids. A wired or wireless communication link between the at least one hearing aid and the auxiliary device is established that allows for exchanging information (e.g. control and status signals, possibly audio signals) between the at least one hearing aid and the auxiliary device. Such auxiliary devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing aid. The remote control is adapted to control functionality and operation of the at least one hearing aids. The function of the remote control may be implemented in a SmartPhone or other electronic device, the SmartPhone/electronic device possibly running an application that controls functionality of the at least one hearing aid.

In general, a hearing aid includes i) an input unit such as a microphone for receiving an acoustic signal from a user's surroundings and providing a corresponding input audio signal, and/or ii) a receiving unit for electronically receiving an input audio signal. The hearing aid further includes a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to enhance a target acoustic source among a multitude of acoustic sources in the user's environment. In one aspect, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The output unit may include an output transducer for providing mechanical vibrations either transcutaneously or percutaneously to the skull bone.

Figure 1A:
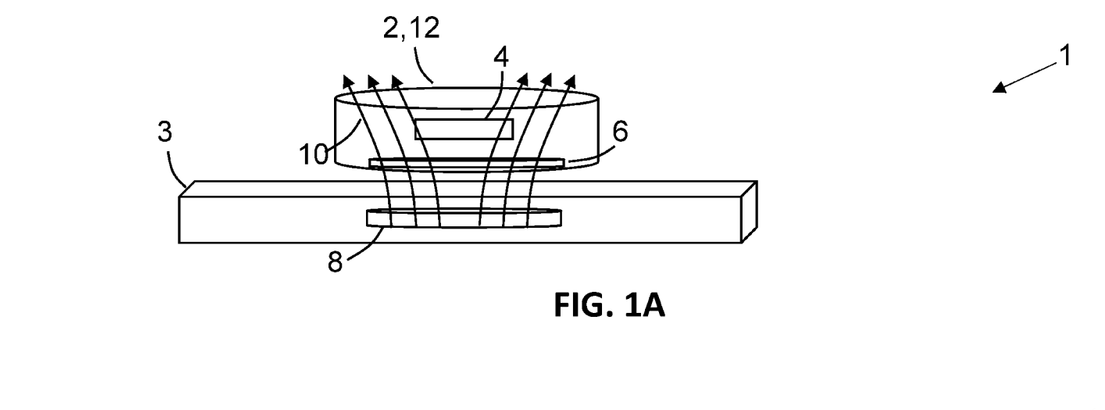
FIGS. 1A and 1B illustrate different examples of an implantable hearing aid system.
Figure 1B:
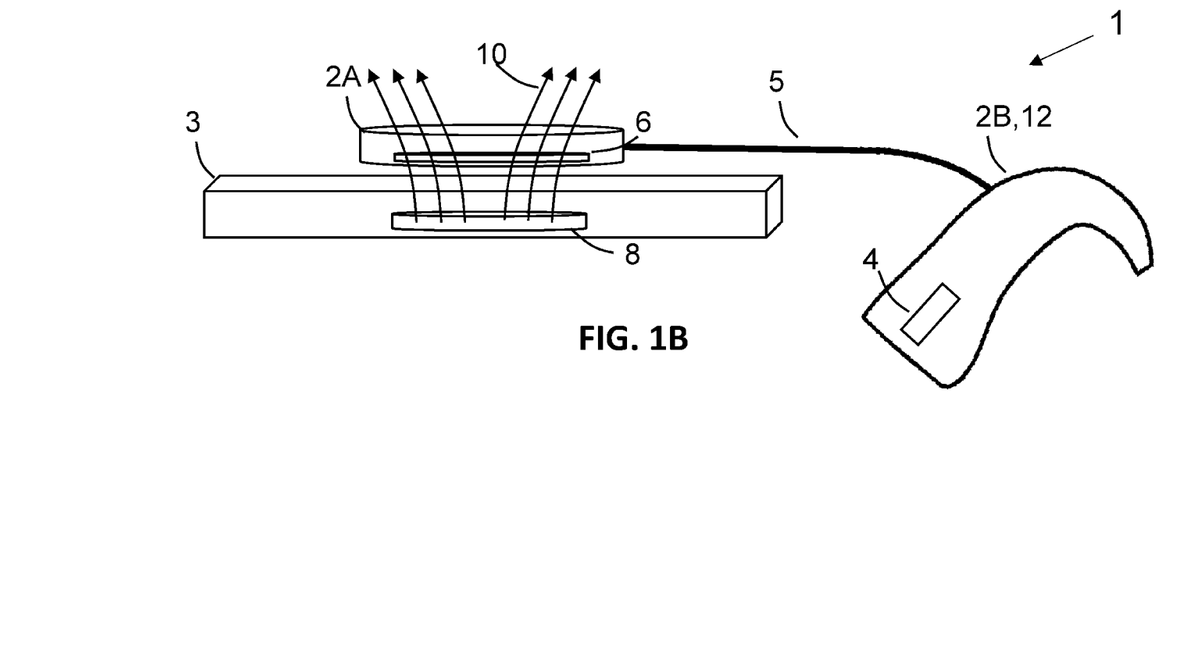

FIGS. 1A and 1B illustrate different examples of an implantable hearing aid system 1, wherein the implantable hearing aid system 1 comprises a charger unit 3 including a coil unit 8 having a first resonance frequency. Furthermore, the system 1 includes a hearing aid (2,2A,2B) which comprises a rechargeable battery 4, an inductive coil arrangement 6 having a second resonance frequency configured to form an inductive charging link 10 with the coil unit 8 to receive power signals from the charger unit 3. Additionally, the system 1 includes an implantable component (not shown) which includes an implantable coil, wherein the inductive coil arrangement is further configured to form a transcutaneous link with the implantable coil to transmit at least one of data and power to the implantable component, and wherein the first resonance frequency and the second resonance frequency are matched or partly matched. In FIG. 1A, the inductive coil arrangement 6 is arranged within a housing 12 of the hearing aid 2, and in FIG. 1B, the inductive coil arrangement 6 is arranged externally to the housing 12 of the hearing aid 2B. In FIG. 1B, the inductive coil arrangement 6 is connected to the housing 12 via a connector part 5 which includes one or more wires for transferring data and power between the inductive coil arrangement 6 and the hearing aid 2B.

Figures 2A, 2B:
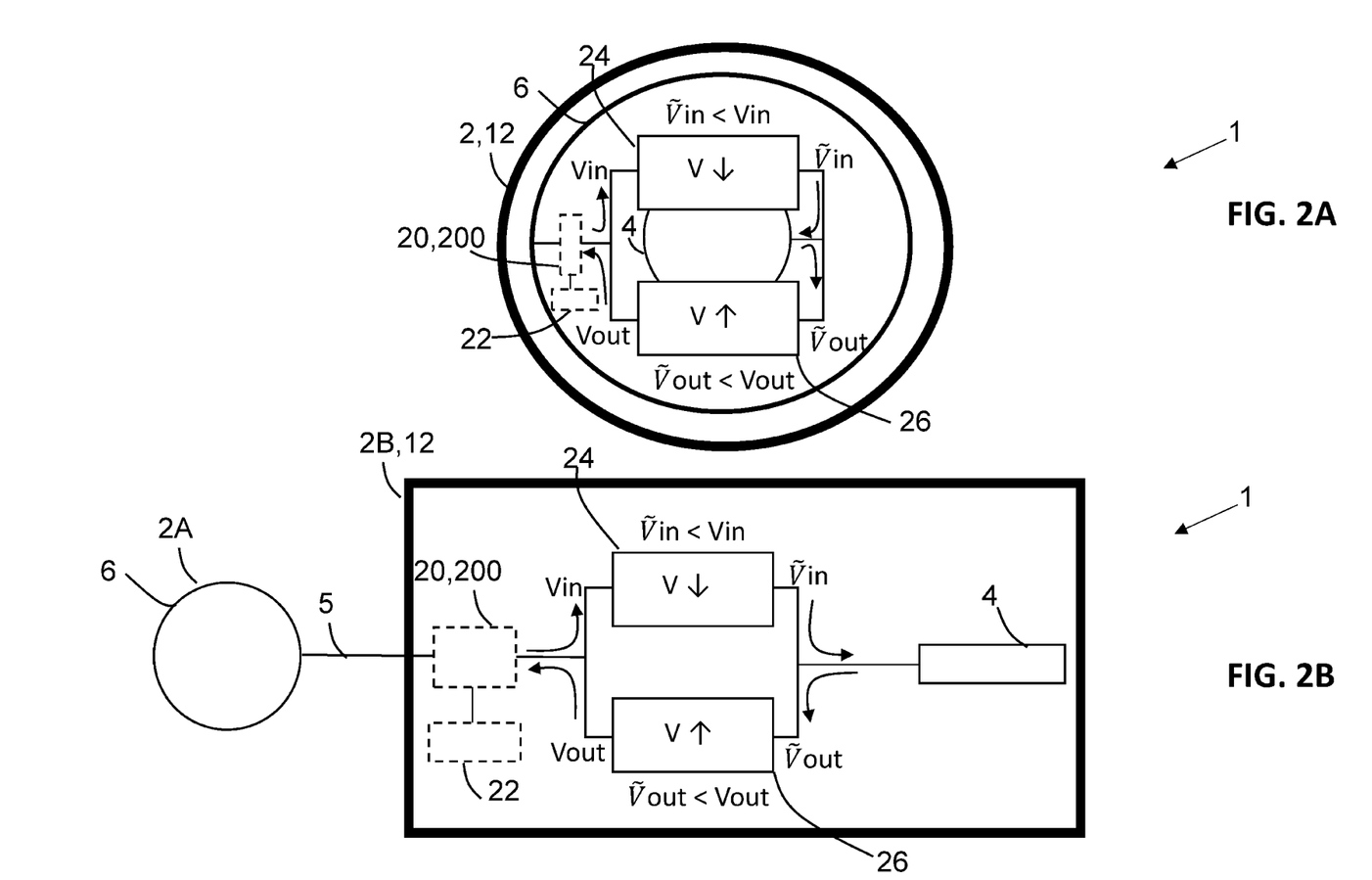
FIGS. 2A to 2B illustrate different examples of an implantable hearing aid system.

FIGS. 2A and 2B illustrate different examples of the implantable hearing aid system 1, wherein the hearing aid (2,2A,2B) includes a voltage decreasing converter 24 configured to decrease a voltage of the power signals received from the charger unit 3 for use in charging the rechargeable battery 4, and a voltage increasing converter 26 configured to increase a voltage of signals obtained from the rechargeable battery 4. In FIG. 2A, at least the rechargeable battery 4, the voltage increasing and decreasing converter (24, 26) are arranged within an area encircled by the inductive coil arrangement 6 or in vicinity to the center of the inductive coil arrangement 6. In FIG. 2B at least the rechargeable battery 4, the voltage increasing and decreasing converter (24, 26) are arranged within a housing 12 of the hearing aid 2B, and the inductive coil arrangement 6 is arranged externally to the housing 12.

In FIGS. 2A and 2B, the hearing aid (2, 2A, 2B) includes a capacitive circuit arrangement (20, 200) configured to adjust the resonance frequency of the inductive coil arrangement to a plurality of resonance frequencies including at least the second resonance frequency and the third resonance frequency.

In FIGS. 2A and 2B, the hearing aid (2, 2A, 2B) includes a processor 22 configured to transmit a control signal to the capacitive circuit arrangement (20,200).

Figure 3A:
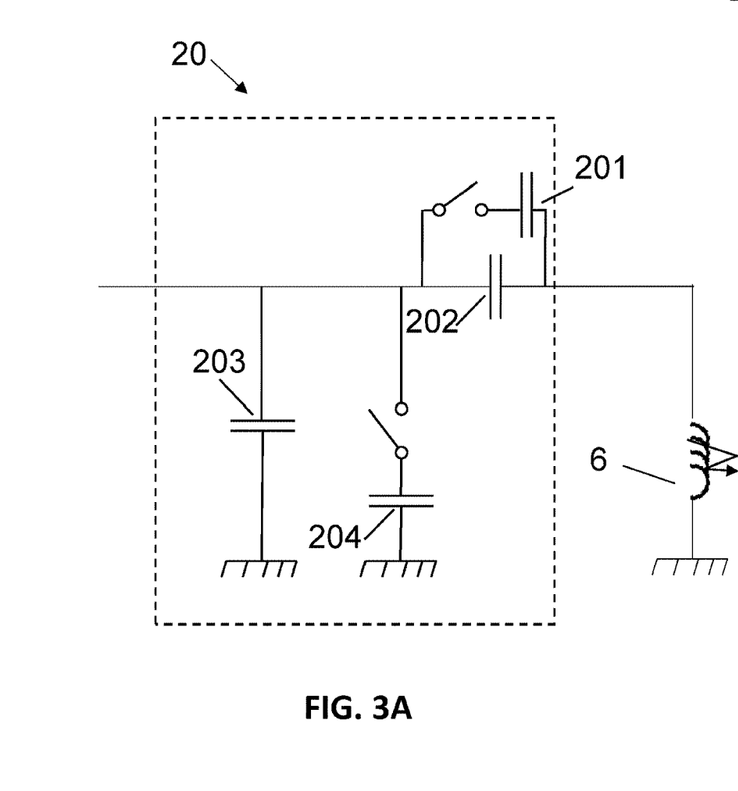
FIGS. 3A and 3B illustrate different examples of a capacitive circuit arrangement.
Figure 3B:
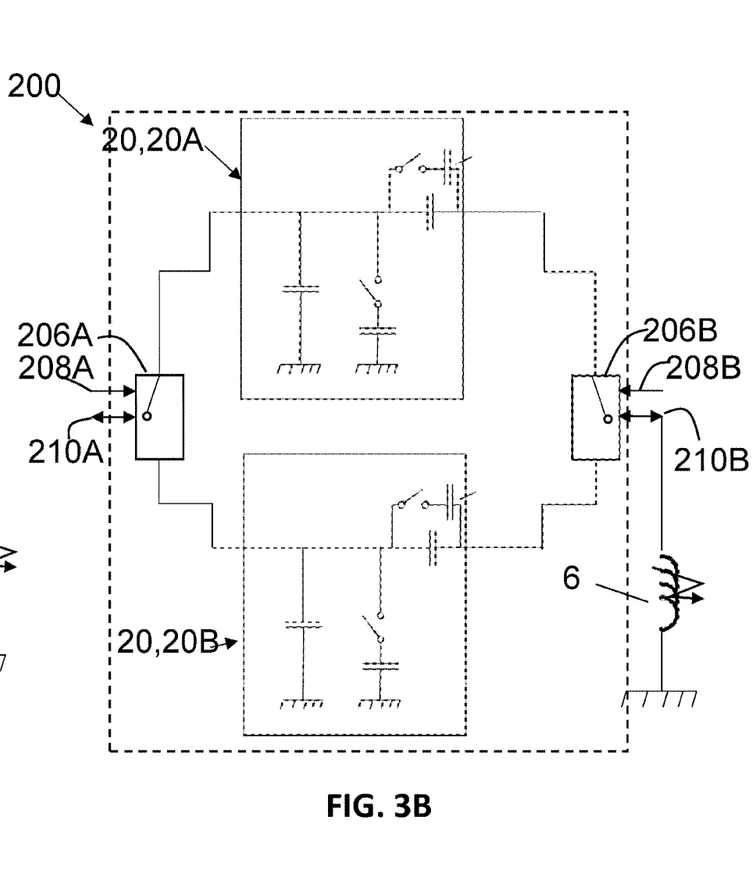

FIGS. 3A and 3B illustrates different examples of the capacitive circuit arrangement (20,200). In FIG. 3A, the capacitive circuit arrangement (20) may include at least one of a first switched capacitor 204 and a second switched capacitor 201, wherein the first switched capacitor 204 may be connected in parallel to a first circuitry element 203, and the second switched capacitor 201 may be connected in serial to a second circuitry element 202. Further, the resonance frequency of the inductive coil arrangement 6 may be adapted based on the at least one measured of a Q factor of the inductive coil arrangement, or based on a power level measure of a signal received by the inductive coil arrangement, and selectively connecting at least one of the first and second switched capacitors 201, 204 to the circuitry constituting the capacitive circuit arrangement (20).

In FIG. 3B, the capacitive circuit arrangement (200) includes at least a switch (206A, 206B), a first tuning circuit (20,20A) and at least a second circuit (20,20B), and each of the two tuning circuits (20,20A,20B) is connected to the switch (206A, 206B). The switch (206A, 206B) is configured to receive a control signal (208A,208B) and connect (210A,210B) the inductive coil arrangement 6 and the remaining parts (4,22) of the hearing aid (2,2A,2B) to either the first tuning circuit (20,20A) or the second tuning circuit (20,20B) based on the control signal (208A,208B).

The first tuning circuit (20,20A) is configured to form the transcutaneous link with the implantable coil (not shown) when connected to the inductive coil arrangement 6 via the switch (206A,206B), and wherein the second tuning circuit (20,20B) is configured to form the inductive charging link 10 with the coil unit 8 when connected to the inductive coil arrangement 6 via the switch (206A,206B).

The control signal may be determined by the processor 22, and the processor is configured to determine the control signal based on a measure of a Q factor of the inductive coil arrangement 6, or the control signal is determined based on a power level measure of a signal received by the inductive coil arrangement 6.

Figure 4A:
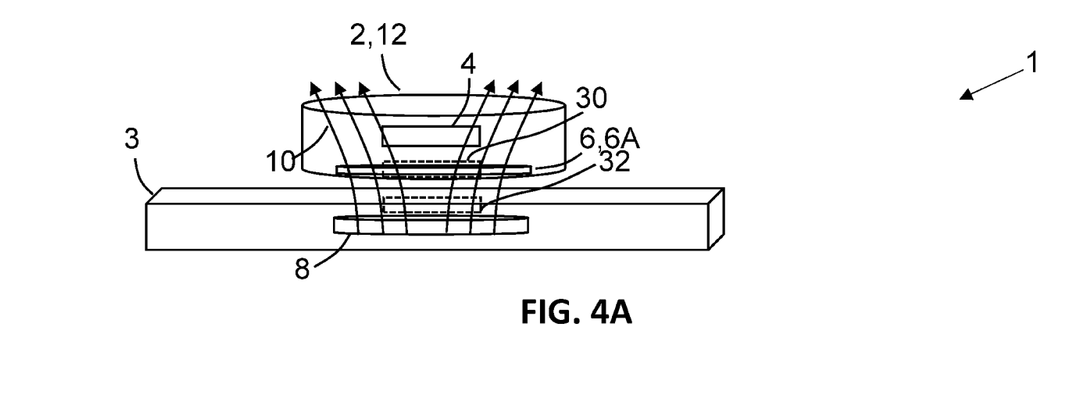
FIGS. 4A and 4B illustrate different examples of an implantable hearing aid system.
Figure 4B:
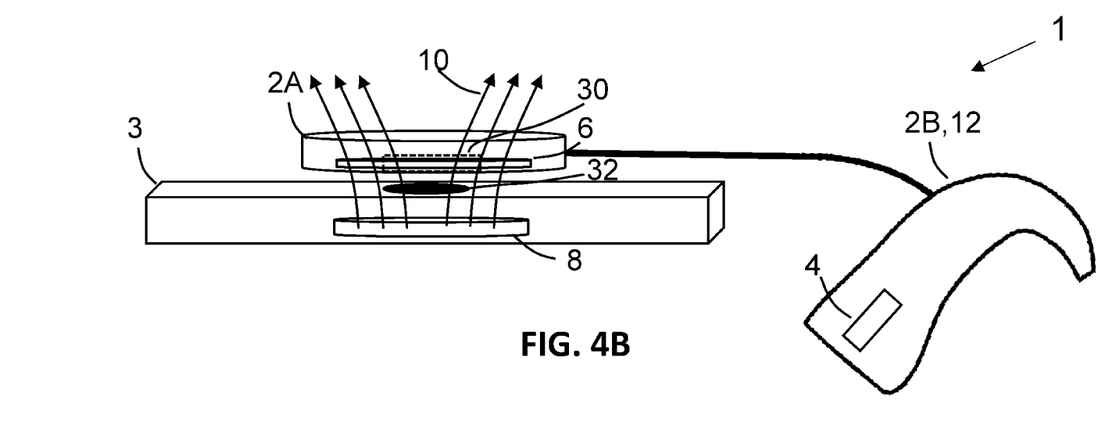

FIGS. 4A and 4B illustrate different examples of the implantable hearing aid system 1, the inductive coil arrangement 6 may include a magnet 30 configured to align an inductive coil 6A of the inductive coil arrangement 6 to the coil unit 8 of the charger unit 3. In FIG. 4A, the charger unit includes a magnet 32 which is arranged such that the coil unit 8 circumference the magnet 32, and the magnet 30 in the inductive coil arrangement 6 is arranged such that the inductive coil 6A circumference the magnet 30.

In FIG. 4B, the charger unit may have a second magnet, a metal surface or a metal component which is configured to magnetically attract the magnet of the inductive coil arrangement. The metal surface or the metal component may be arranged in a center of the coil unit 8, and coils of the coil unit 8 form circumferences centered at the center of the coil unit 8.

Figure 5:
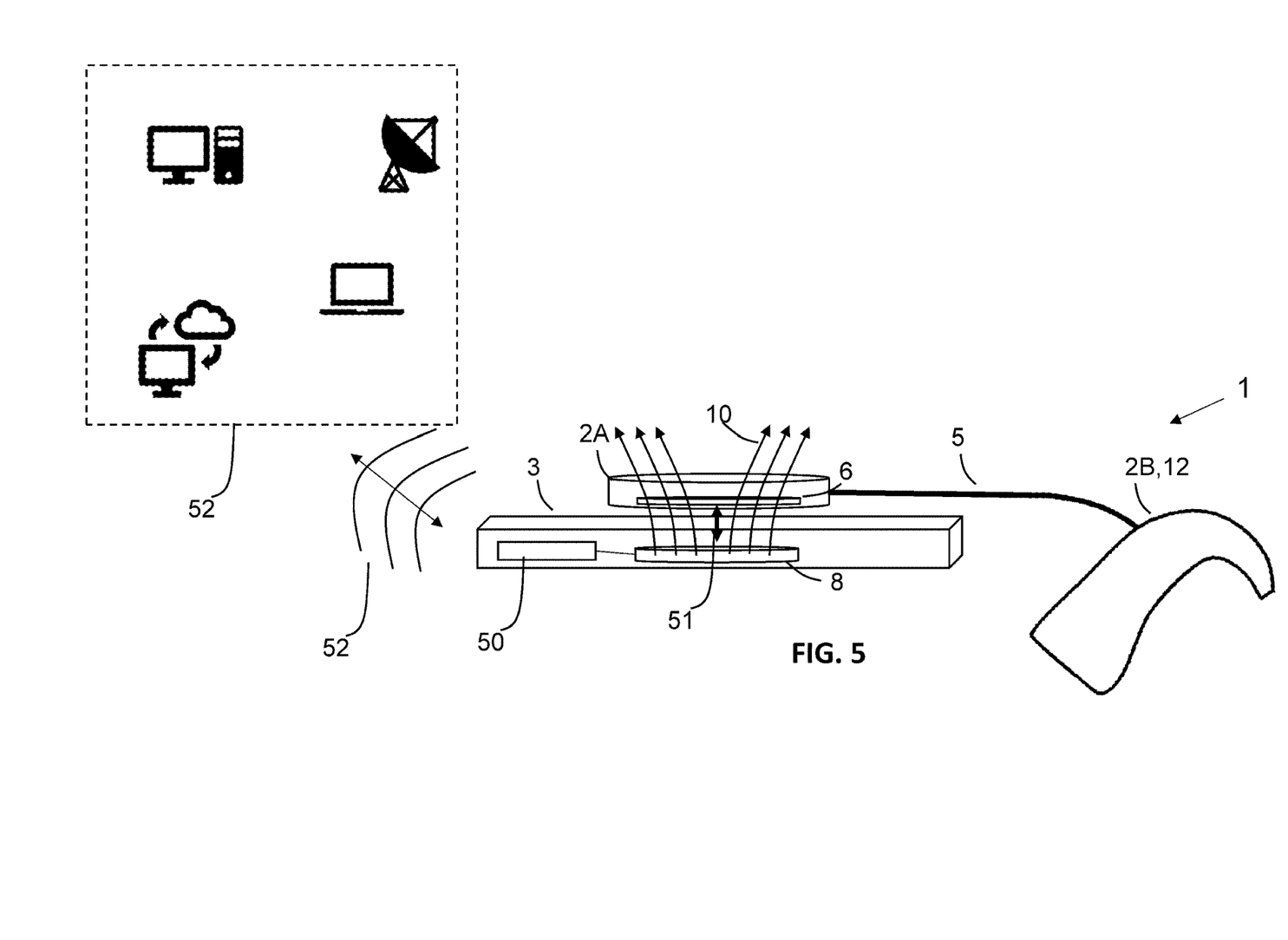
FIG. 5 illustrate an example of an implantable hearing aid system.

FIG. 5 illustrate the implantable hearing aid system 1, where the charger unit 3 is configured to transmit data to the hearing aid via the inductive charging link 10 or via a second inductive link 51 between the coil unit 8 and the inductive coil arrangement 6, and wherein the transmitted data includes charging data, software update data and/or firmware update data.

The charger unit 3 may include a far-field communication interface 50 configured to transmit an update acknowledgement signal via the far-field communication interface 50, and, to receive software update data and/or firmware update data via the far-field communication interface 50 based on the update acknowledgement signal.

The far-field communication interface 50 includes a transceiver interface configured for transmitting and receiving software update data via a communication network 52, and wherein the communication network 52 includes mobile network, a local network and/or a wireless network.

The local network may include one or more of Bluetootk, Bluetooth Low energy, WIFI etc.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, elements, components, and/or steps but do not preclude the presence or addition of one or more other features, elements, components, and/or steps thereof. It will also be understood that when an element is referred to as being "connected" or "coupled" to another element, it can be directly connected or coupled to the other element, but an intervening element may also be present, unless expressly stated otherwise. As used herein, the term "and/or" includes any and all combinations of one or more of the associated listed items. The steps of any disclosed method are not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The scope should be judged in terms of the claims that follow.

The invention claimed is:

1. An implantable hearing aid system, comprising:
   a charger unit including a coil unit having a first resonance frequency,
   a hearing aid, including:
      a rechargeable battery,
      an inductive coil arrangement having a second resonance frequency configured to form an inductive charging link with the coil unit to receive power signals from the charger unit,
      a voltage decreasing converter configured to decrease a voltage of the power signals received from the charger unit for use in charging the rechargeable battery, and
      a voltage increasing converter configured to increase a voltage of signals obtained from the rechargeable battery, and
   an implantable component including an implantable coil, wherein the inductive coil arrangement is further configured to form a transcutaneous link with the implantable coil to transmit at least one of data and power to the implantable component, and wherein the first resonance frequency and the second resonance frequency are substantially the same and within a frequency range of between 80 kHz to 300 kHz, wherein the hearing aid further comprises a capacitive circuit arrangement configured to adjust the resonance frequency of the inductive coil arrangement to a plurality of resonance frequencies including at least the second resonance frequency via a respective tuning circuit, and wherein the signals obtained from the rechargeable battery, whose voltage is increased by the voltage increasing converter, are used for transmission of the at least one of data and power to the implantable component via the inductive coil arrangement and the transcutaneous link.

2. The implantable hearing aid system according to claim 1, wherein the first resonance frequency and the second resonance frequency are selectively limited to a frequency range of between 110 kHz and 205 kHz.

3. The implantable hearing aid system according to claim 2, wherein the inductive coil arrangement includes a magnet configured to align an inductive coil of the inductive coil arrangement to the coil unit of the charger unit.

4. The implantable hearing aid system according to claim 2, wherein the inductive coil arrangement having a third resonance frequency being in resonance to a resonance frequency of the implantable coil.

5. The implantable hearing aid system according to claim 1, wherein the inductive coil arrangement includes a magnet configured to align an inductive coil of the inductive coil arrangement to the coil unit of the charger unit.

6. The implantable hearing aid system according to claim 1, wherein the inductive coil arrangement having a third resonance frequency being in resonance to a resonance frequency of the implantable coil.

7. The implantable hearing aid system according to claim 6, wherein the third resonance frequency is within a frequency range of 4 MHz to 6.5 MHz, 4 MHz to 10 MHz, or 4 MHz to 12 MHz.

8. The implantable hearing aid system according to claim 1,
wherein the hearing aid includes a processor configured to transmit a control signal to the capacitive circuit arrangement, and
wherein the capacitive circuit arrangement includes a switch, a first tuning circuit, and a second tuning circuit, each of the first and second tuning circuits being connected to the switch, and the switch is configured to receive the control signal, and
wherein the switch is configured to connect the inductive coil arrangement to either the first tuning circuit or the second tuning circuit based on the control signal.

9. The implantable hearing aid system according to claim 8, wherein the first tuning circuit is configured to form the transcutaneous link with the implantable coil when connected to the inductive coil arrangement via the switch, and wherein the second tuning circuit is configured to form the inductive charging link with the coil unit when connected to the inductive coil arrangement via the switch.

10. The implantable hearing aid system according to claim 8, wherein the control signal is determined based on a measure of a Q factor of the inductive coil arrangement, or the control signal is determined based on a power level measure of a signal received by the inductive coil arrangement.

11. The implantable hearing aid system according to claim 1, wherein the hearing aid includes a first antenna configured to form a communication link to a second antenna of the charger unit for communicating charging data.

12. The implantable hearing aid system according to claim 11, wherein the charging data includes charge capacity information or temperature of the rechargeable battery.

13. The implantable hearing aid system according to claim 1, wherein the charger unit is configured to transmit data to the hearing aid via the inductive charging link or via a second inductive link between the coil unit and the inductive coil arrangement, and wherein the transmitted data includes charging data, software update data and/or firmware update data.

14. The implantable hearing aid system according to claim 13,
wherein the plurality of resonance frequencies includes a fourth resonance frequency for the second inductive link.

15. The implantable hearing aid system according to claim 13, wherein the charger unit includes a far-field communication interface configured to transmit an update acknowledgement signal via the far-field communication interface, and, to receive software update data and/or firmware update data via the far-field communication interface based on the update acknowledgement signal.

16. The implantable hearing aid system according to claim 15, wherein the update acknowledgement signal includes information data about the hearing aid.

17. The implantable hearing aid system according to claim 15, wherein the far-field communication interface includes a transceiver interface configured for transmitting and receiving software update data via a communication network, and wherein the communication network includes mobile network, a local network and/or a wireless network.

* * * * *